United States Patent [19]

Bernatowicz et al.

[11] 4,347,622
[45] Aug. 31, 1982

[54] SIGNATURE SURVEILLANCE OF NUCLEAR FUEL

[75] Inventors: Henry Bernatowicz, Fremont, Calif.; Frederick C. Schoenig, Jr., Wilmington, N.C.

[73] Assignee: General Electric Company, San Jose, Calif.

[21] Appl. No.: 137,592

[22] Filed: Apr. 7, 1980

[51] Int. Cl.³ .................. G21C 17/00; G01R 33/16
[52] U.S. Cl. ............................ 376/245; 376/257; 324/201
[58] Field of Search .............. 176/19 R, 58 PB; 324/201, 228, 239, 236; 376/245, 257

[56] References Cited

U.S. PATENT DOCUMENTS 3,801,002  5/1974  Sata .................................. 324/236
4,243,939  1/1981  Grossman et al. ................. 324/228

FOREIGN PATENT DOCUMENTS 14729    3/1980  European Pat. Off. .
1362530  8/1974  United Kingdom .
1362731  8/1974  United Kingdom ............ 176/58 PB
1547371  6/1979  United Kingdom .
2010492  6/1979  United Kingdom .

Primary Examiner—Sal Cangialosi
Attorney, Agent, or Firm—Ivor J. James, Jr.; Samuel E. Turner; Raymond G. Simkins

[57] ABSTRACT

Typical nuclear fuel material contains tramp ferromagnetic particles of random size and distribution. Also, selected amounts of paramagnetic or ferromagnetic material can be added at random or at known positions in the fuel material. The fuel material in its nonmagnetic container can be scanned by magnetic susceptibility change detecting apparatus to provide a unique signal waveform of the container of fuel material as a signature thereof. At subsequent times in its life, the container similarly can be scanned to provide subsequent signatures. Comparison of the signatures reveals any alteration or tampering with the fuel material.

22 Claims, 4 Drawing Figures

SIGNATURE SURVEILLANCE OF NUCLEAR FUEL

BACKGROUND OF THE INVENTION

This invention relates to a method for surveillance of the nuclear fuel in fuel elements and fuel bundles to detect any diversion of the nuclear material therefrom.

Typically nuclear fuel, such as uranium or plutonium oxide, is in the form of pellets or powder contained in a suitable container such as an elongated cladding tube sealed by end plugs to form a fuel element as shown, for example, in U.S. Pat. No. 3,378,458.

As typically used in a nuclear reactor core, a number of fuel elements are supported in spaced array between upper and lower tie plates to form a separately replaceable fuel assembly or bundle as shown, for example, in U.S. Pat. No. 3,689,358. A sufficient number of such fuel bundles are arranged in a matrix, approximating a right circular cylinder, to form the nuclear reactor core capable of self-sustained fission reaction. Periodically the core is refueled by replacement of some of the fuel bundles to restore the necessary reactivity. Thus the fuel bundle is the normal unit of fuel material transfer and use throughout the fuel cycle. That is, the fuel elements are assembled into bundles at the fuel fabrication factory. The bundles are shipped to the reactor and placed in the core. Eventually the bundles are removed from the core and stored as such or are shipped to a reprocessing plant.

An object of this invention is to provide a method and apparatus for obtaining a unique indication or signature of individual fuel elements and individual fuel bundles at any point in the fuel cycle to assure that the fuel material therein has not been removed or otherwise tampered with. Another object is to provide nondestructive surveillance of nuclear fuel elements and bundles.

SUMMARY

This invention is based upon the known fact that nuclear fuel contains varying amounts (typically in the order of several hundred parts per million) of tramp ferromagnetic particles, particularly particulate iron, primarily from oxidative corrosion and abrasion of the fuel processing equipment.

This invention is based further on the recognition that the ferromagnetic particle distribution (that is, the sizes of the particles, the amount or number of particles and the location of the particles) is random. Hence the ferromagnetic particle distribution is unique for each fuel element and for each bundle of fuel elements. These randomly distributed ferromagnetic particles cause changes in magnetic susceptibility proportional to the changes in the ferromagnetic particle content as the fuel element or fuel bundle is passed through a constant or direct current magnetic field.

If desired, known amounts of ferro or paramagnetic material could be added at random or at known positions in the fuel material. This added magnetic material could be used to augment the tramp magnetic material and, especially if placed in known positions could be used to provide, for example, type identification of the fuel material.

Thus in accordance with the invention the fuel element or fuel bundle is passed through a sensing coil in a constant magnetic field and the signals produced by the sensing coil, due to changes in magnetic susceptibility caused by the changing ferromagnetic particle content, are recorded to provide a unique signature of the particular fuel element or fuel bundle. At any subsequent time the particular fuel element or fuel bundle similarly can be scanned again whereby the subsequent signature thus obtained can be compared to the originally recorded signature to determine whether or not any fuel material in such fuel element or fuel bundle has been removed or otherwise tampered with.

If the fuel material contains an additive, such as a burnable neutron absorber, with high paramagnetic susceptibility and in varying amounts along the length of the fuel element or fuel bundle, the contribution of such paramagnetic material to the signature signal can be determined and separated from the contribution of the ferromagnetic material. The fuel element or fuel bundle is passed through two different constant magnetic fields of different strengths and the differential susceptibility changes in the two different magnetic fields is determined. For some applications it may be desirable to obtain and record the signature signals of both the ferromagnetic and paramagnetic material.

The fuel surveillance method of the invention provides the outstanding advantage of requiring no changes in the fuel element or fuel bundle design or composition.

DRAWING

DESCRIPTION

Apparatus has been disclosed previously, in U.S. Pat. No. 4,243,939 issued Jan. 6, 1981, which is incorporated by reference herein, for determining the paramagnetic additive content and the ferromagnetic impurity content of nuclear fuel rods. Similar apparatus can be employed in the practice of the method of this invention to provide the desired magnetic signature signals due to the randomly distributed tramp ferromagnetic particles in nuclear fuel elements or bundles of fuel elements.

Figure 1:
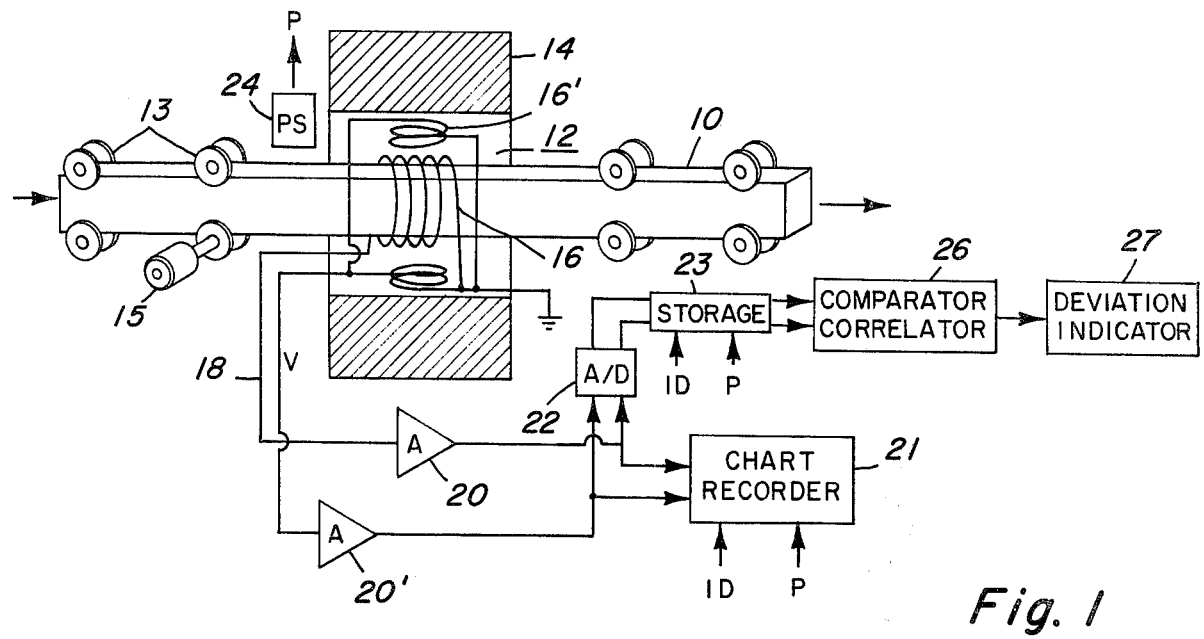
FIG. 1 is a schematic illustration including a magnet and associated circuitry in accordance with a first embodiment of apparatus for practice of the method of the invention.

Shown in FIG. 1 is apparatus for providing the magnetic signature of a body or container 10 of nuclear fuel. The container 10 may be a single fuel element formed of a sealed cladding tube of nonmagnetic material containing the nuclear fuel material. Or the container 10 may be a bundle of fuel elements held in spaced array by suitable tie or end plates and intermediate spacers. (Ordinarily the spacers are formed of nonmagnetic material, however, if any components thereof, such as springs, are formed of magnetic material, such components will cause susceptibility change signals which simply become a part of the fuel bundle signature.)

To scan the container 10 to provide its magnetic signature signal, the container 10 is moved through a sensing coil 16 positioned in the opening or bore 12 of an annular magnet 14 which produces a constant or direct current magnetic field. The container 10 can be driven and guided through the sensing coil 16 by any suitable devices such as wheels or rollers 13, one or more of which are driven by a motor 15.

Figure 2:
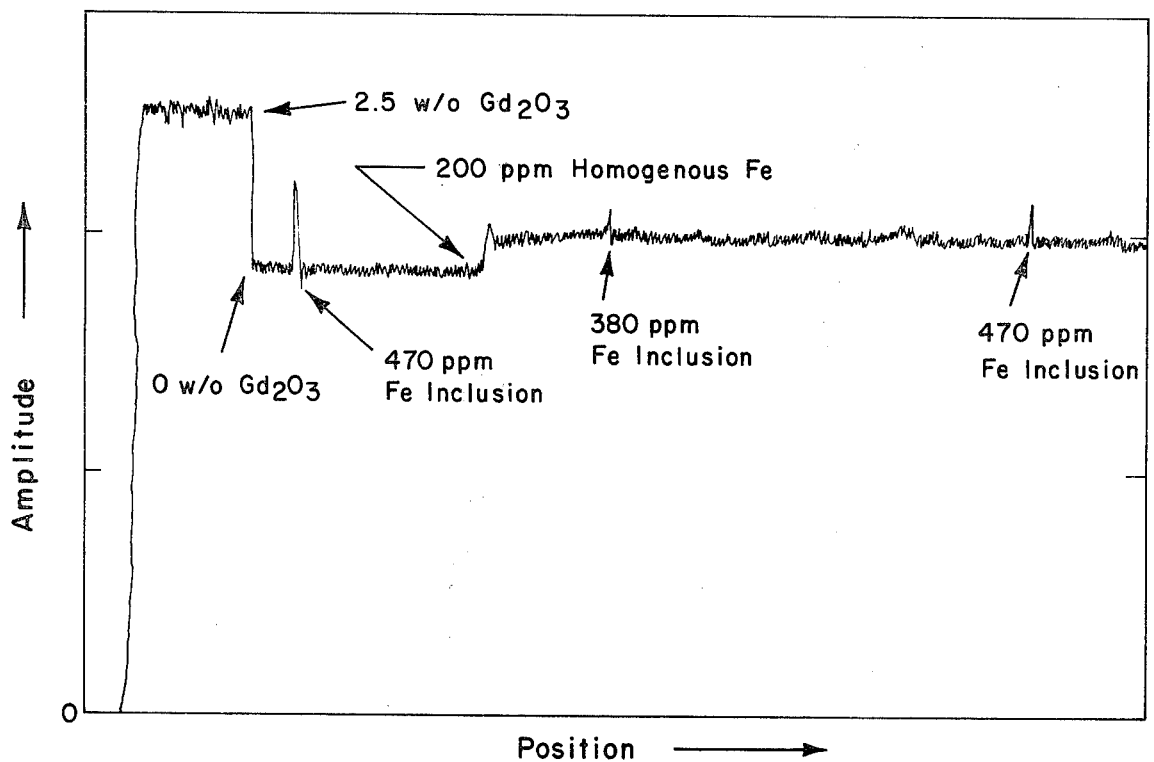
FIG. 2 illustrates a typical initial signature waveform of a fuel element.

As the container 10 moves therethrough, the coil 16 produces a voltage V which is proportional to the product of the change in susceptibility dX times N (the number of turns of coil 16) times H (the field strength of the magnet 14 in the region of coil 16). The voltage developed by sensing coil 16 is applied over a lead 18 to an amplifier 20 and thence to a well-known indicating and recording device such as a strip or chart recorder 21 to thus record the waveform of the voltage with respect to time of movement of the container 10 through the sensing coil 16 as a signature of the material in the container. A representative waveform 17 as the magnetic signature of a single fuel element is illustrated in FIG. 2.

The signal from amplifier 20 also (or alternatively) may be applied through an analogue-to-digital converter 22 to a suitable digital signal storage device 23 (for example, a magnetic tape storage device). In addition to the signature signal, ordinarily it will be desirable to enter therewith in the recorder 21 and storage device 23 an identification signal ID corresponding to a serial number or other unique identification symbol of the container 10.

Also, it may be desirable to index the signature waveform 17 with respect to one or more points along the length of the container 10. For this purpose one or more container position sensors 24 may be positioned along the path of the container, the sensor 24 being of the well-known photo-electric or other suitable type.

As an alternative, or in addition to the sensing coil 16, a split sensing coil 16′ may be provided and positioned such that the longitudinal axis of its winding is transverse to the longitudinal axis of the container 10. The sensing coil 16′ thus provides an alternative or additional susceptibility change signature signal which is applied to an amplifier 20′ and thence to the chart recorder 21 and analogue-to-digital converter 22.

It is contemplated that the first scan of the container 10, to provide its initial or first signature, will be made at the fuel manufacturing factory. It is further contemplated that similar signature producing apparatus will be provided at the nuclear reactor plants and at fuel storage and reprocessing facilities by which the container 10 will be scanned at appropriate subsequent times such as upon receipt at the reactor site, upon removal from the reactor core and upon receipt at storage or reprocessing facilities. The subsequent signatures thus obtained then will be compared to the initial signature to reveal any alteration or tampering with the material in the container 10.

Signature waveforms produced by strip or chart recorder 21 can be compared visually. Signature waveforms stored in digital form in storage device 23 can be converted to suitable visual form for comparison (as by digital-to-analogue conversion and recording on a strip chart).

Alternatively the signature waveforms stored in storage device 23 can be compared automatically by the provision of a comparison-correlation device 26. The two waveform signals to be compared are called from storage in storage device 23 and simultaneously applied to the comparison-correlation device 26. Deviation of one signal from the other may be registered by a deviation indicator 27.

The prolonged exposure of the fuel material in container 10 to the high temperature and high radiation of a nuclear reactor core may cause a decrease in the magnetic susceptibility of the tramp ferromagnetic particles in the fuel material. Therefore, when the container 10 is scanned after being removed from the reactor core, the amplitudes of the susceptibility change signal caused by the ferromagnetic particles may be lower, thereby giving a signature waveform of lower amplitude peaks. However, if there has been no alteration or tampering with the fuel material, the general shape of the signature waveform (the relative amplitudes, shapes and positions of the peaks and valleys of the signal) will not have changed. Thus the comparison-correlation device 26 should be of the type which compares the shapes and positions of the waveforms and not their amplitudes. A suitable device for use as such a comparison-correlation device 26 is a suitably programmed Digital Equipment Corp. PDP 11-34 computer.

For high sensitivity the sensing coil 16 of the scanning apparatus of FIG. 1 should comprise a large number of turns (e.g. 1000) consistent with available space and minimization of resistance of the winding.

Figure 3:
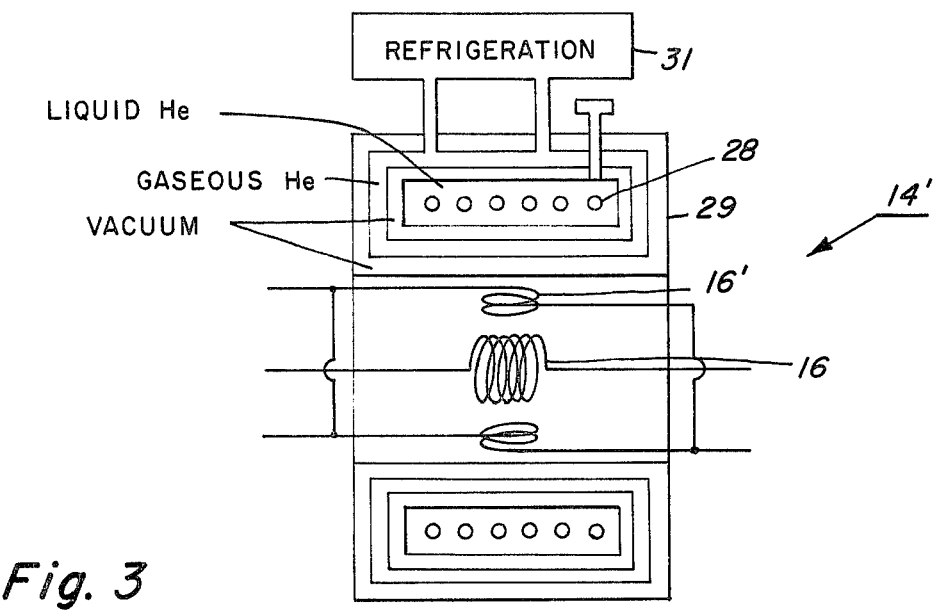
FIG. 3 is a schematic illustration of a superconductive magnet.

The magnet 14 may be an ordinary electromagnet or a permanent magnet which can provide field strengths up to about 10 KOe. For higher field strengths a superconductive solenoid or electromagnet can be used. A superconductive magnet 14′ is illustrated in FIG. 3. Such magnets have been described, for example, by V. L. Newhouse in "Applied Superconductivity," John Wiley & Sons, Inc., New York, 1964. Typically the superconducting magnet 14′ comprises a coil 28 formed of a superconductive material such as niobium-titanium connected as a persistent current loop and maintained at a superconductive temperature by liquid helium contained in a compartmented, vacuum insulated container or Dewar 29 cooled by a refrigeration unit 31. Such superconductive magnetics are available, for example, from Intermagnetics General Corporation, Guilderland, N.Y.

If the fuel material in container 10 contains a strongly paramagnetic additive such as gadolinium, a burnable neutron absorber or poison, it may be desirable to separate the contribution of the additive to the susceptibility change signals from that of the ferromagnetic material as the container is scanned. As discussed in the aforementioned copending U.S. Pat. No. 4,243,939 (issued Jan. 6, 1981), such burnable absorber is usually distributed in varying amounts from zone to zone along the length of the container. Its magnetic response can be used as additional information with regard to identification if desired.

Apparatus for scanning a fuel material container 10′ containing a paramagnetic additive to provide a signature waveform due to ferromagnetic particles therein ith different field strengths.

Positioned within the bores of magnets 32 and 33 are respective sensing coils 37 and 38 which may be similar to the coil 16 of FIG. 1. A container 10′ to be scanned (containing nuclear fuel, a paramagnetic additive and ferromagnetic particles) is moved at a constant velocity through the sensing coils 37 and 38 whereby changes in susceptibility of the material produce respective output signals $V_1$ and $V_2$ on respective leads 41 and 42.

The signal $V_1$ on lead 41 is applied to a delay 43. The delay 43 delays the signal $V_1$ from coil 37 so that it appears at the output of the delay coincident in time with the signal $V_2$ from the same increment of container 10'. The delay 43 is preferably adjustable so that its delay time can be correlated with the velocity of the container 10' through the sensing coils 37 and 38. (A suitable such delay is available, for example, from Reticon Corporation, Sunnyvale, Calif. as shown in their brochure No. 57324.)

The delayed signal $V_1$, at the output of delay 43, is applied through a gain-controlled amplifier 44 to one input of a differential amplifier 46 while the signal $V_2$ is applied through a gain-controlled amplifier 47 to the other input of differential amplifier 46.

The gain-controlled amplifiers modify the levels of the signals $V_1$ and $V_2$ in accordance with predetermined constants $K_3$ and $K_4$ of the system whereby (as more fully described hereinafter), the contribution of the paramagnetic additive to the signal is subtracted so that the difference signal I at the output of differential amplifier 46 is proportional to the ferromagnetic content of the fuel material.

The strengths of both magnets 32 and 33 should be high to maximize sensitivity. On the other hand, their strengths are desirably significantly different to provide a practical level of the difference signal I. A ratio of strengths of about two is found practical. For example, the magnet 32 may have a field strength of about 60 KOe and the magnet 33 a field strength of about 30 KOe.

The difference signal I, which is directly proportional to ferromagnetic material content is related to the constants $K_3$ and $K_4$ and voltages $V_1$ and $V_2$ as follows:

$$I = K_3 V_1 - K_4 V_2 \quad (1)$$

$K_3$ and $K_4$ are constants of the system which, suitably determined, result in elimination of the contribution to the signal I of the paramagnetic additive.

For a given system and system operating conditions, $K_3$ and $K_4$ most readily are determined empirically, for example, in the following manner: At least two test containers 10' are needed, each of which contains an accurately known change in the ferromagnetic content along its length. (Or a single element could be used having known ferromagnetic content change at two suitably separated locations along its length.) For accuracy of determination of $K_3$ and $K_4$ the ferromagnetic content changes in the two test segments should be significantly different.

The first test container is passed through the coils 37 and 38, at the predetermined container velocity of the system, and a first set of voltages $V_1$ and $V_2$, on leads 41 and 42, resulting from the change in ferromagnetic content in the container is measured. The second test container is then passed through the coils 37 and 38 and a second set of the resulting voltages $V_1$ and $V_2$ is similarly measured. These two sets of numerical values for the signals $V_1$ and $V_2$ and the corresponding known numerical values of the known ferromagnetic content are inserted in the relationship (1) above. This provides two equations from which numerical values for $K_3$ and $K_4$ can be determined. The gain-controlled amplifiers 44 and 47 then can be adjusted to represent the numerical values of $K_3$ and $K_4$. Accuracy in the determination of $K_3$ and $K_4$ can be improved by using additional test containers of known ferromagnetic content change.

The ferromagnetic content signal I may be applied to recorder 21 and/or storage device 23 for display and recording of the container signature waveform for subsequent use as discussed hereinbefore in connection with the arrangement of FIG. 1.

Figure 4:
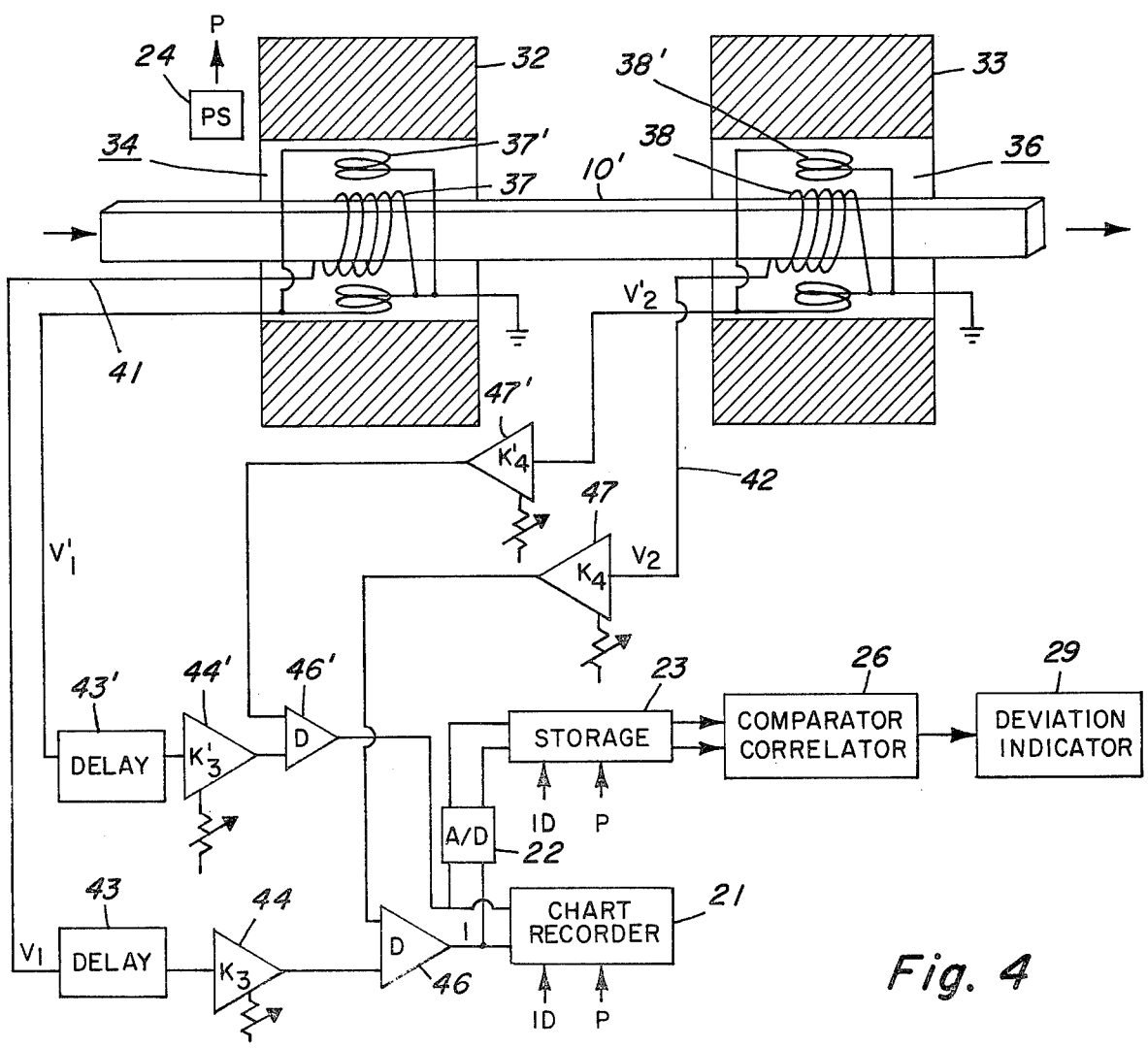
FIG. 4 is a schematic illustration of a pair of magnets and associated circuitry in accordance with a second embodiment of apparatus for practice of the method of the invention.

As in the embodiment of FIG. 1, alternative or addition sensing coils 37' and 38', positioned with their longitudinal axes transverse to the longitudinal axis of the container 10', may be provided in the embodiment of FIG. 4. Signal $V_1'$ from the sensing coil 37' is applied through a delay 43' and a gain controlled amplifier 44' to differential amplifier 46'. The signal $V_2'$ from sensing coil 38' is similarly applied to differential amplifier 46' through a gain controlled amplifier 47'. The output signal from differential amplifier 46' is applied to the analogue-to-digital converter 22 and chart recorder 21 to record the signature waveform produced from the sensing coils 37' and 38'. The constants $K_3'$ and $K_4'$ can be determined in the manner described hereinbefore with respect to the constants $K_3$ and $K_4$.

We claim:

1. A method for surveillance of nuclear fuel material in an elongated fuel material containing container, wherein said fuel material includes distributed ferromagnetic particles, comprising the steps of:
   (1) providing apparatus for scanning said container to produce susceptibility change signals indicative of changes in magnetic susceptibility of said material along the length of said container due to said ferromagnetic particles;
   (2) performing a first scan along the length of said container at a given time in its life to produce a first susceptibility change signal as a first signature of said fuel material containing container;
   (3) recording said first signature;
   (4) performing a second scan along the length of said container at a subsequent time in its life to produce a second susceptibility change signal as a second signature of said fuel material containing container; and
   (5) comparing said second signature to said first signature whereby similarity of the signatures indicates absence of tampering.

2. The method of claim 1 wherein said fuel material containing container is a fuel bundle.

3. The method of claim 1 wherein said fuel material containing container is a fuel element.

4. A method for surveillance of nuclear fuel material in an elongated fuel material container, wherein said fuel material includes distributed ferromagnetic particles and a paramagnetic additive varying in amount along the length of the container, comprising the steps of:
   (1) providing apparatus for scanning said container to produce susceptibility change signals indicative of changes in magnetic susceptibility of said material along the length of said container and including means for subtracting the contribution of said paramagnetic additive to said susceptibility change signals;
   (2) performing a first scan along the length of said container at a given time in its life to produce a first susceptibility change signal due to said ferromagnetic particles as a first signature of said fuel material containing container;
   (3) recording said first signature;
   (4) performing a second scan along the length of said container at a subsequent time in its life to produce a second susceptibility change signal due to the ferromagnetic particles in the fuel material therein as a second signature of said fuel material containing container; and
(5) comparing said second signature to said first signature whereby similarity of the signatures indicates absence of tampering.

5. The method of claim 4 wherein said fuel material containing container is a fuel bundle.

6. The method of claim 4 wherein said fuel material containing container is a fuel element.

7. A method for surveillance of nuclear fuel material in an elongated non-magnetic fuel material containing container, wherein said fuel material includes distributed ferromagnetic particles, comprising the steps of:
(1) establishing a direct current magnetic field having a strength of at least 1000 Gauss;
(2) disposing inductive means in said magnetic field for producing signals indicative of changes in direct current susceptibility of material moved adjacent thereto;
(3) performing a scan along the length of said container at a given time in its life by moving said container adjacent said inductive means at a given velocity whereby said inductive means produces a signal varying in amplitude with time in accordance with the distribution of said ferromagnetic particles in said fuel material;
(4) recording said signal as a first signature of said fuel material containing container;
(5) providing a second signature of said fuel material containing container at a subsequent time in its life by repetition of steps (1)–(3); and
(6) comparing said second signature to said first signature whereby similarity of the signatures is indicative of the absence of tampering with said fuel material.

8. The method of claim 7 wherein said fuel material containing container is a fuel bundle.

9. The method of claim 7 wherein said fuel material containing container is a fuel element.

10. The method of claim 7 wherein said inductive means comprises a sensing coil and said container is moved through said sensing coil.

11. The method of claim 10 wherein the signal produced by said sensing coil is amplified and recorded with respect to time of movement of said container through said coil.

12. The method of claim 7 wherein said magnetic field has a strength in the range of 1000 to 100,000 Gauss.

13. The method of claim 12 wherein said magnetic field is established by a superconductive magnet.

14. The method of claim 7 wherein said velocity is from about 1 to about 100 feet per minute.

15. The method of claim 7 wherein said fuel material is a compound selected from the group consisting of oxides of uranium, plutonium, thorium and mixtures thereof.

16. A method for surveillance of nuclear fuel material in an elongated, non-magnetic fuel material containing container, wherein said fuel material includes distributed ferromagnetic particles and a paramagnetic additive varying in amount along the length of the container, comprising the steps of:
(1) establishing first and second direct current magnetic fields of different field strengths greater than about 1000 Gauss;
(2) disposing in each magnetic field respective first and second inductive means for producing signals indicative of changes in susceptibility of material moved adjacent thereto;
(3) performing a scan along the length of said container at a given time in its life by moving said container adjacent said first and second inductive means in sequence whereby each of said inductive means produces a signal varying in amplitude with time in accordance with changes in magnetic susceptibility of said material;
(4) processing the signals from said first and second inductive means to subtract the contribution of said paramagnetic additive to said signals and to provide a resulting signal varying in amplitude with time in accordance with the distribution of said ferromagnetic particles in said material as a first signature of said fuel material containing container;
(5) recording said first signature of said fuel material containing container;
(6) providing a second signature of said fuel material containing container at a subsequent time in its life by repeating steps (1)–(4); and
(7) comparing said second signature to said first signature whereby similarity of the signatures is indicative of the absence of tampering with said fuel material.

17. The method of claim 16 wherein said fuel material containing container is a fuel bundle.

18. The method of claim 16 wherein said fuel material containing container is a fuel element.

19. The method of claim 16 wherein said processing includes adjusting the magnitude of the signals from said first and second inductive means in accordance with respective constants $K_3$ and $K_4$ and determining the sum of the magnitudes of the adjusted first and second signals from the same successive incremental portions of said container to provide said resulting signal.

20. The method of claim 19 wherein $K_3$ and $K_4$ are constants of the scanning system determined by scanning at least two containers containing material having known different ferromagnetic content.

21. A method for surveillance of a paramagnetic material in an elongated material containing container wherein said material includes ferromagnetic particles distributed therein, comprising the steps of:
(1) providing apparatus for scanning said container to produce susceptibility change signals indicative of changes in magnetic susceptibility of said material along the length of said container due to the distribution of said ferromagnetic particles;
(2) performing a first scan along the length of said container at a given time in its life to produce a first susceptibility change signal as a signature of said fuel material containing container;
(3) recording said first signature; and
(4) performing at least one subsequent scan along the length of said container at subsequent times in its left to produce susceptibility change signals as subsequent signatures of said fuel material containing container whereby significant differences in a subsequent signature from said first signature are indicative of tampering with said material.

22. A method for surveillance of a body of non-ferromagnetic material which includes ferromagnetic particles distributed therein, comprising the steps of:
(1) providing apparatus for scanning said body to produce susceptibility change signals indicative of changes in magnetic susceptibility of said material along the length of said body due to the distribution of said ferromagnetic particles;
(2) performing a first scan along the length of said body at a given time in its life to produce a first susceptibility change signal as a signature of said body;
(3) recording said first signature;
(4) performing at least one subsequent scan along the length of said body at subsequent times in its life to produce susceptibility change signal as subsequent signatures of said body whereby significant differences in a subsequent signature from said first signature are indicative of tampering with said material.

* * * * *